(12) United States Patent
DeRenzo

(10) Patent No.: US 6,823,345 B2
(45) Date of Patent: Nov. 23, 2004

(54) METHOD AND SYSTEM FOR EVALUATING AND ENHANCING MEDICAL ETHICAL INFORMATION FLOW IN HEALTH CARE ORGANIZATIONS

(76) Inventor: Evan G. DeRenzo, 4 Grovepoint Ct., Rockville, MD (US) 20854

( * ) Notice: Subject to any disclaimer, the term of this patent is extended or adjusted under 35 U.S.C. 154(b) by 480 days.

(21) Appl. No.: 09/850,108

(22) Filed: May 8, 2001

(65) Prior Publication Data

US 2002/0169621 A1 Nov. 14, 2002

(51) Int. Cl.⁷ .............................................. G06F 17/30
(52) U.S. Cl. ........................................ 707/104.1; 705/2
(58) Field of Search .......................... 705/2, 3; 707/5, 707/10, 104.1

(56) References Cited

U.S. PATENT DOCUMENTS

| | | | | |
|---|---|---|---|---|
| 4,858,354 A | * | 8/1989 | Gettler | ........................ 40/324 |
| 5,247,661 A | * | 9/1993 | Hager et al. | .............. 707/104.1 |
| 5,867,821 A | * | 2/1999 | Ballantyne et al. | ............ 705/2 |
| 6,449,598 B1 | * | 9/2002 | Green et al. | .................... 705/2 |

* cited by examiner

*Primary Examiner*—Jack M Choules
(74) *Attorney, Agent, or Firm*—Dickstein Shapiro Morin & Oshinsky LLP

(57) ABSTRACT

The present invention is a method of evaluating the flow of medical ethical information within a health care organization. The dissemination practices of the health care organization are determined, so that a process map can be generated. This process map is used to pinpoint problems with the information flow of medical ethical information within the health care organization. New policies and/or procedures are devised to alleviate the problems and the hospital's personnel is trained in the implementation of the new policies and/or procedures.

12 Claims, 5 Drawing Sheets

METHOD AND SYSTEM FOR EVALUATING AND ENHANCING MEDICAL ETHICAL INFORMATION FLOW IN HEALTH CARE ORGANIZATIONS

FIELD OF THE INVENTION

The present invention involves a method and system for evaluating and enhancing the flow of medical ethical information flow in health care organizations.

BACKGROUND OF THE INVENTION

Health care organizations (i.e. community hospitals, Harvard Medical School, Washington Hospital Center, free-standing nursing homes, etc.) must disseminate ethics information from a variety of outside sources at varying levels of depth and scope. There are many different types of sources for ethical information. There are federal, state, county and municipal regulations; codes of ethics; ancient norms of medical ethics (e.g. the Hippocratic oath); standards set by accreditation boards, case law, national commissions, policies and procedures, and finding sources requirements.

There are four different areas of medical ethics: 1) clinical ethics; 2) organizational ethics; 3) legal risk management compliance; and 4) research ethics (human and animal). The only standards in place for any of these areas prior to WWII were the ancient norms of medical ethics and those set by professional associations. When the extensive human experimentation that the Nazi's performed was discovered after WWII, the Nuremberg Code was written. The Nuremberg Code was the first major code of ethics for medical research. The Nuremberg Code, did not allow any medical research without a patients voluntary consent. By definition, this completely ruled out research on children and the mentally challenged.

The next major international guidance document directing and guiding the ethics of human research was the declaration of Helsinki. The World Medical Association wrote the first declaration of Helsinki in 1965. The declaration of Helsinki, like the Nuremberg Code, carry substantial authority and was subsequently incorporated into many international regulations.

After Nuremberg and Helsinki, the United States government and the medical establishment assumed that its doctors were not violating any ethical guidelines. Therefore, the Nuremberg and Helsinki remained only guidelines until the Tuskegee Study was revealed in 1974. The Tuskegee Study involved a study of leaving syphilis untreated in African-American male subjects, Public disclosure of the study caused a public outrage. As a consequence, a great deal of attention was paid to research ethics to insure that such experiments would not be repeated.

In addition to attention paid to research ethics, there is attention paid to each of the other three areas. Each area has a variety of codes, ethics and rules applied to it including federal, state, county and municipal (sometimes) regulations, codes of ethics, ancient norms of medical ethics, standards set by accreditation boards, case law, policies and procedures, national commissions and funding sources.

A health care organization receives information applicable to its functions from many different sources. Each source may have a different entry point to the health care organization; some may have multiple entry points. Lists of who should receive ethical information are generally kept by each sector that is an entry point. Unfortunately, these lists are often inaccurate or simplistic.

Much of the above material is sent to department heads to decide who else needs to see it. Department heads often neglect to disseminate important information because they do not have the time to sift through all of the information, disagree with the information, or overlook important points altogether.

The major problem with this method of distribution is that the amount of information that each department head receives is enormous. Only a small portion of what they receive is important for each department. In addition, of the small portion that is important for each department, different people (i.e. nurses, doctors, etc.) will need to review and understand different portions of it. For example, rather than each person receiving the few pages of pertinent information, the department head receives 400 pages that he or she does not have time to sift through in order to determine what to distribute and what is important to each person who needs it.

As a result of the above, the task of distributing the appropriate material to the appropriate people within health care organizations requires a detailed understanding of how medical ethical information is distributed within the health care organization and a way to modify that method. Thus, there exists a need in the art for a method of evaluating and enhancing medical ethical information flow at health care organizations.

BRIEF SUMMARY OF THE INVENTION

The present invention is a method of evaluating and improving the flow of medical ethical information within a health care organization. The dissemination practices of the health care organization are determined, so that a process map can be generated. This process map is used to pinpoint problems with the information flow of medical ethical information with the health care organization. New policies and/or procedures are devised to alleviate the problems and the hospital's personnel is trained in the implementation of the new policies and/or procedures.

It is, therefore, an object of the present invention to provide a method of evaluating and improving the medical ethical information dissemination practices of health care organizations.

It is further an object of the present invention to provide a method of evaluating the flow of medical ethical information within a health care organization by determining the functions of said health care organization; determining what medical ethical information the health care organization must distribute; determining which disciplines and which functions should receive each piece of medical ethical information; determining what information each individual is actually receiving; determining the current dissemination practices; and generating a process map of the current dissemination practices.

It is another object of the present invention to use the process map to improve the dissemination practices.

It is further an object of the present invention that the dissemination practices are evaluated to determine if any problems that are illustrated in the process map can be alleviated within the health care organization's current policies and procedures or if the policies and procedures are the problem.

It is yet another object of the present invention that if the policies and procedures are determined to be the problem, the policies and procedures are modified.

It is another object of the present invention that the health care organization's personnel are educated and trained to implement the modified policies and procedures.

It is further an object of the present invention that if the problems can be alleviated within the health care organization's current policies and procedures, additional procedures are devised to alleviate the problem.

It is yet another object of the present invention that the health care organization's personnel are trained to implement the additional procedures.

It is another object of the present invention to provide a system for evaluating the flow of medical ethical information within a health care organization comprising a microprocessor, a user interface, a display, and a data storage area. The data storage area stores medical ethical information classified by discipline and function.

If is further an object of the present invention that when a request for medical ethical information for a specific discipline and function is entered into the user interface, the microprocessor retrieves the corresponding information from the data storage area and displays the information.

It is yet another object of the present invention that the data storage area stores discipline and function information for health care organization employees.

It is another object of the present invention that when new medical ethical information, and its corresponding discipline and function classification, are entered into the data storage area, the microprocessor automatically displays a distribution list for the new information.

It is further an object of the present invention that the data storage area stores medical ethical information classified by discipline, function, and geographical location.

Other objects and advantages of the present invention will be readily apparent from the following description and drawings which illustrate the present invention.

DETAILED DESCRIPTION OF THE INVENTION

In the following detailed description, reference is made to the accompanying drawings that form a part hereof, and in which is shown by way of illustration specific embodiments of the invention. These embodiments are described in sufficient detail to enable those skilled in the art to practice the invention. It is to be understood that structural changes may be made and equivalent structures substituted for those shown without departing from the spirit and scope of the present invention.

The invention comprises a method and system for evaluating and enhancing medical ethical information flow in health care organizations.

Figure 1:
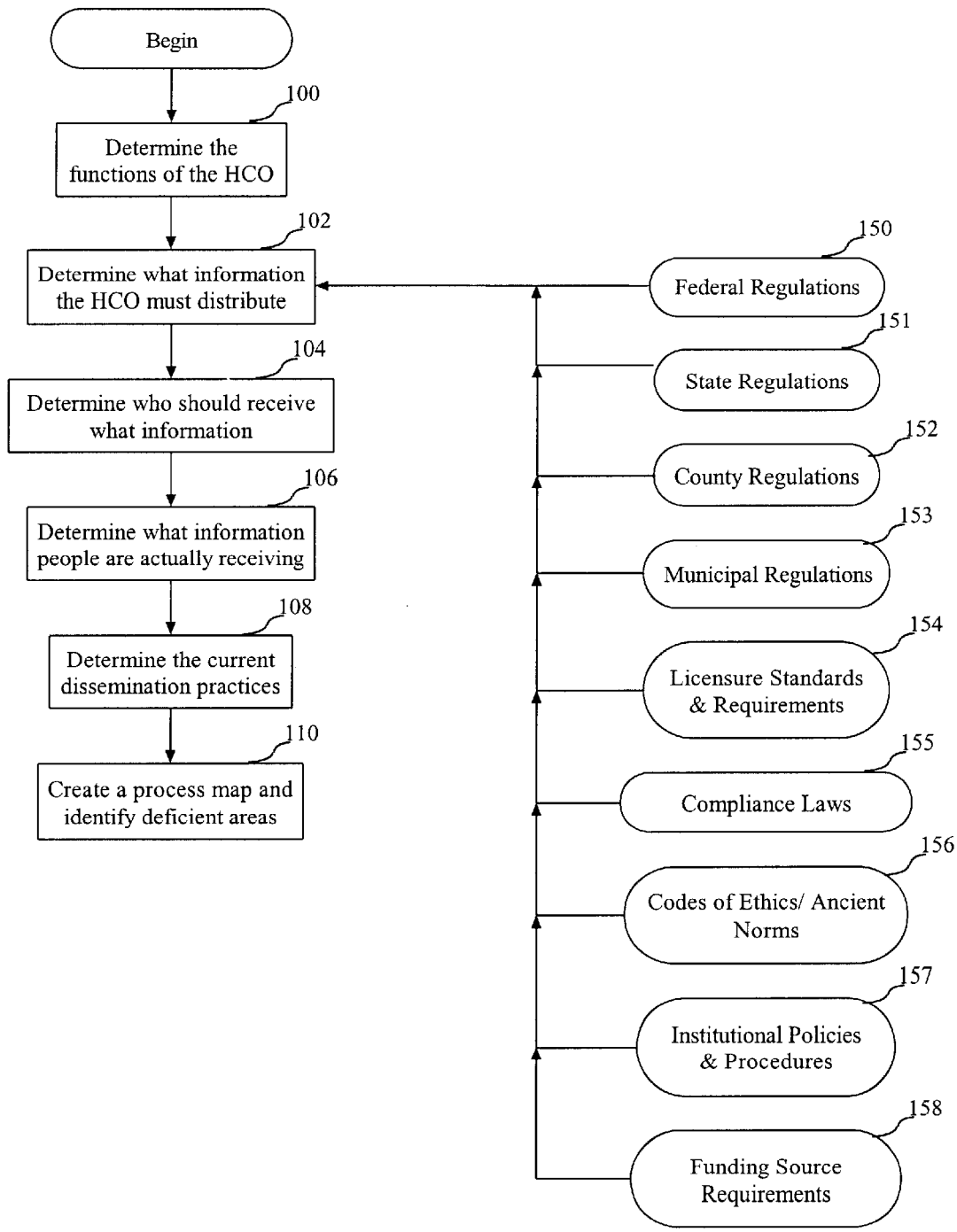
FIG. 1 is a flowchart of a first iteration evaluating a health care organization.

In a preferred embodiment of the present invention, a process map, generated by evaluating a health care organization's ("HCO") current medical ethical information flow in successive iterations of increasing detail focusing on more discrete issues each time, is used to develop better methods of disseminating medical ethical information. The first examination of a health care organization's medical ethical information flow, as shown in FIG. 1, is very broad and begins with determining the functions of the health care organization 100. A nursing home does not require the same medical ethical information to be distributed as a full service hospital.

The following functions can be performed as manual process steps, automated process steps implemented by a computer program, or as part of a system embodied in computer hardware logic elements.

Once the functions of an HCO are determined 100, the information that the HCO should distribute to its employees must be determined 102. The information that must be distributed comes from a variety of different sources, such as, federal regulations 150, state regulations 151, county regulations 152, municipal regulations 153, licensure standards and requirements 154, compliance laws 155, codes of ethics/ancient norms of medical ethics 156, institutional policies and procedures 157, and funding source requirements 158.

After the universe of information that the HCO should be distributing to its employees is determined 102, the universe of information must be broken up according to who should receive each piece of information 104. Each person working in a hospital can digest the medical ethical information easier if they only receive what they should.

Figure 5:
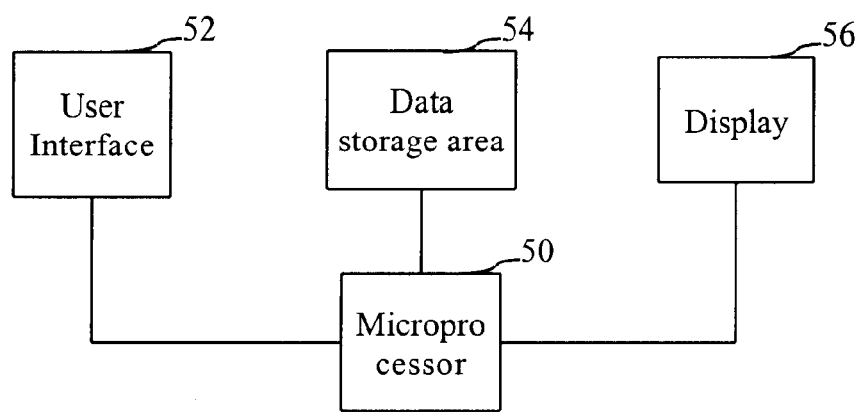
FIG. 5 is a block diagram of a system for evaluating and enhancing medical information flow in health care organizations.

The information that is classified can be stored for future use in a computer system, as shown in FIG. 5. Each piece of medical ethical information is entered into the data storage area 54 through the user interface 52. Once all of the information is entered into the data storage area 54, a discipline and function can be entered into the user interface 52 and a list of medical ethical information for that discipline and function will be displayed 56 by the microprocessor 50 or can be printed out.

Next, it is important to determine what information the employees are actually receiving 106. This step not only entails finding out what they actually receive, but also what else is received with it. If an ICU nurse receives a 400-page binder of information that pertains to all disciplines in the ICU, it may be difficult to discern which parts apply to the nurse, and which parts do not.

After "what" the employees are actually receiving is determined 106, the HCO's current dissemination practices must be traced 108. This entails determining the HCO's entry points of medical ethical information and tracing the information that is disseminated.

The final step in the first iteration is to create a high-level, general process map of the medical ethical information flow 110. This process map, showing how medical ethical information moves around the HCO from when it enters until it stops. This process map can show an efficient system of transferring the appropriate medical ethical information from the entry points to the employees who require it, a disastrous congestion and confusion of information leaving some people with no medical ethical information while others receive too much information, or anywhere in between.

The process map is created using one of the interactive process map generating software products. This process map will illustrate the path that each type of medical ethical information follows from its entry point until it reaches its destination (correct or incorrect). Modifications in an HCO's policies and/or procedures can be input into a completed process map to view the effects prior to implementing any changes.

Figure 2:
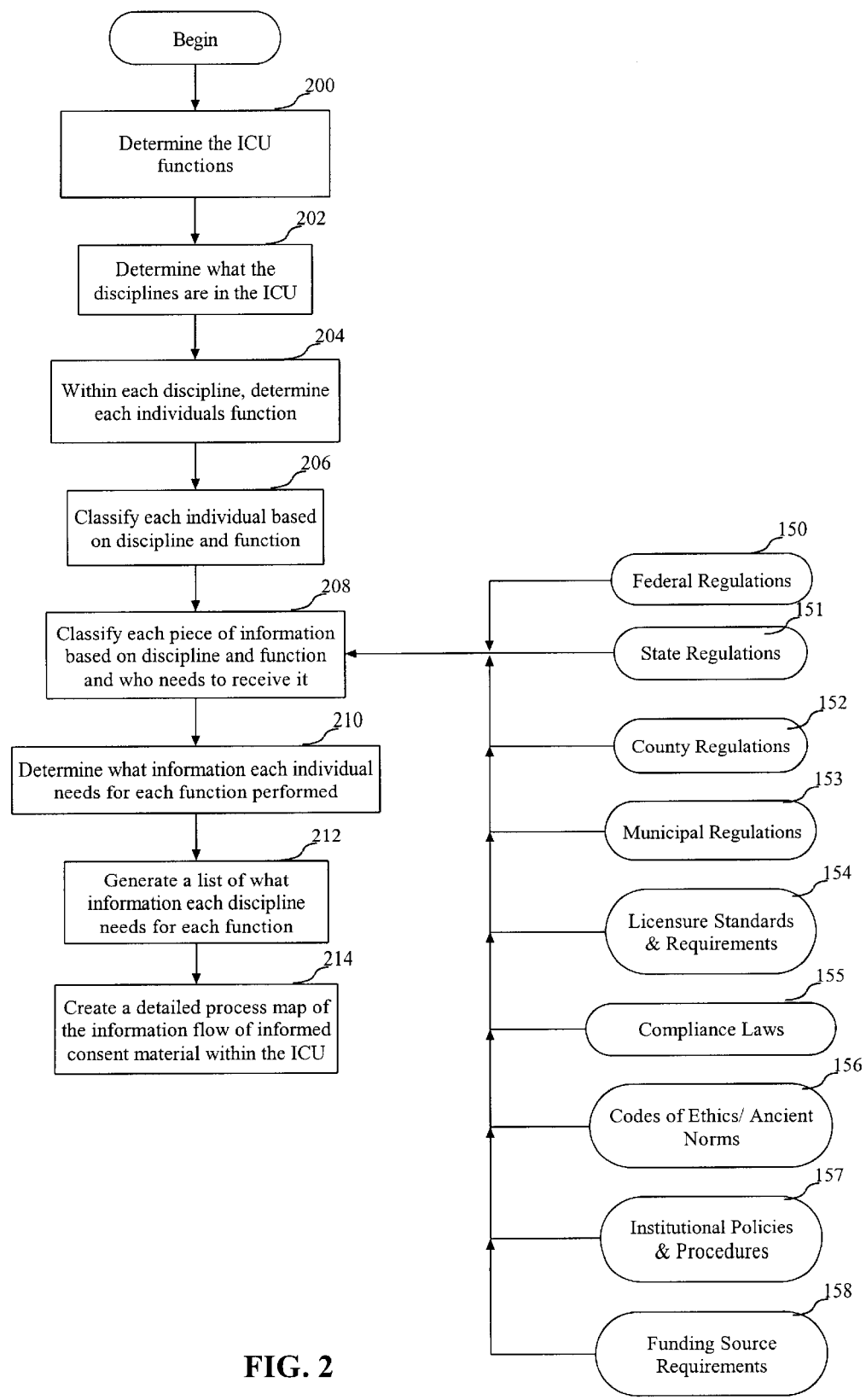
FIG. 2 is a flowchart of a second iteration evaluating the dissemination of informed consent information within the ICU.

If a HCO decides to continue the process in order to obtain greater detail to more effectively address the problems illustrated in the initial process map, the process described above is followed for a specific medical ethical issue for a specific unit of the health care organization, as shown in FIG. 2.

For this second iteration, if the issue being addressed is medical ethical information regarding informed consent in the ICU, the first step would be to determine what the functions of the ICU are 200. Once the functions of the ICU are determined 200, the disciplines within the ICU must be determined 202 and each individual's function within each discipline 204.

Next, each individual must be classified based upon their discipline and function 206. In addition, each piece of information must be classified based on the discipline and function that need to receive it 208. Each individual may have multiple functions within the ICU. The medical ethical information is classified based on discipline and function to determine which individuals should get each piece of information based on the functions he performs 210 by cross-referencing the two sets of classifications. Once this is accomplished, a list is generated of what information each discipline in the ICU needs for each function 212.

Figure 3:
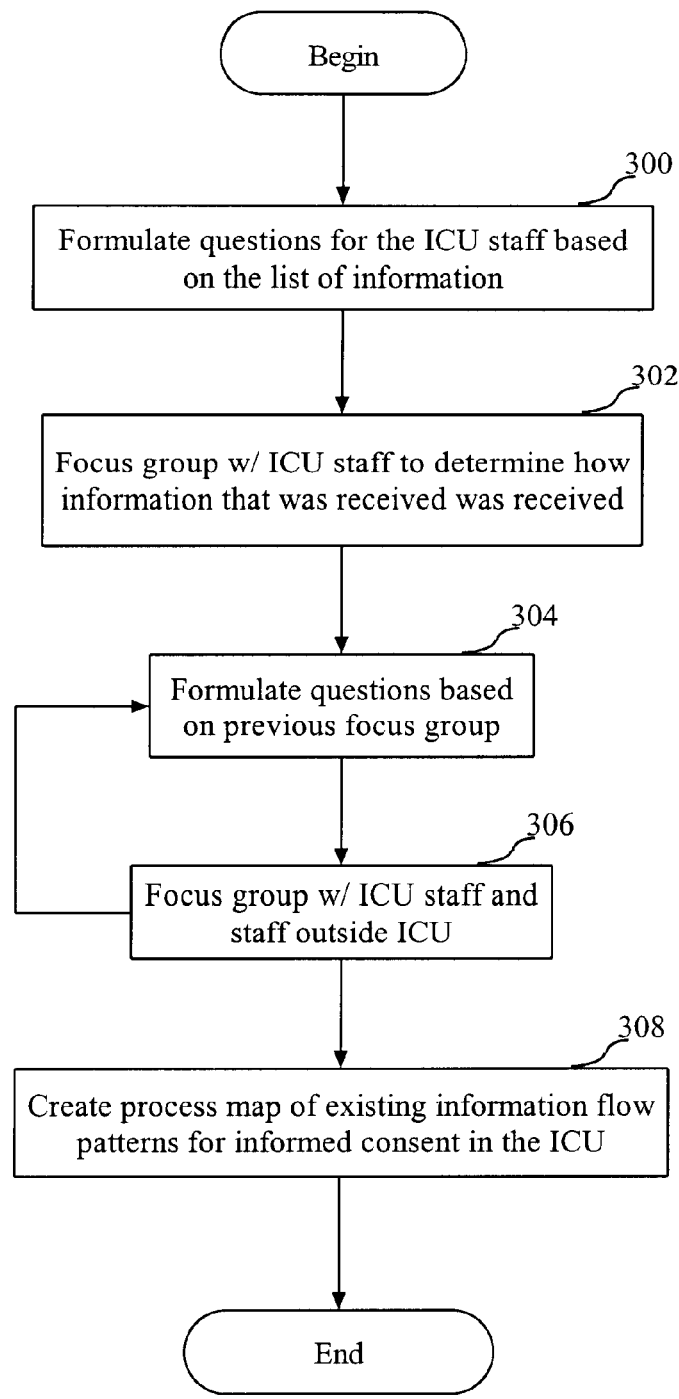
FIG. 3 is a flowchart of the method of determining the current dissemination practices of the ICU.
Figure 4:
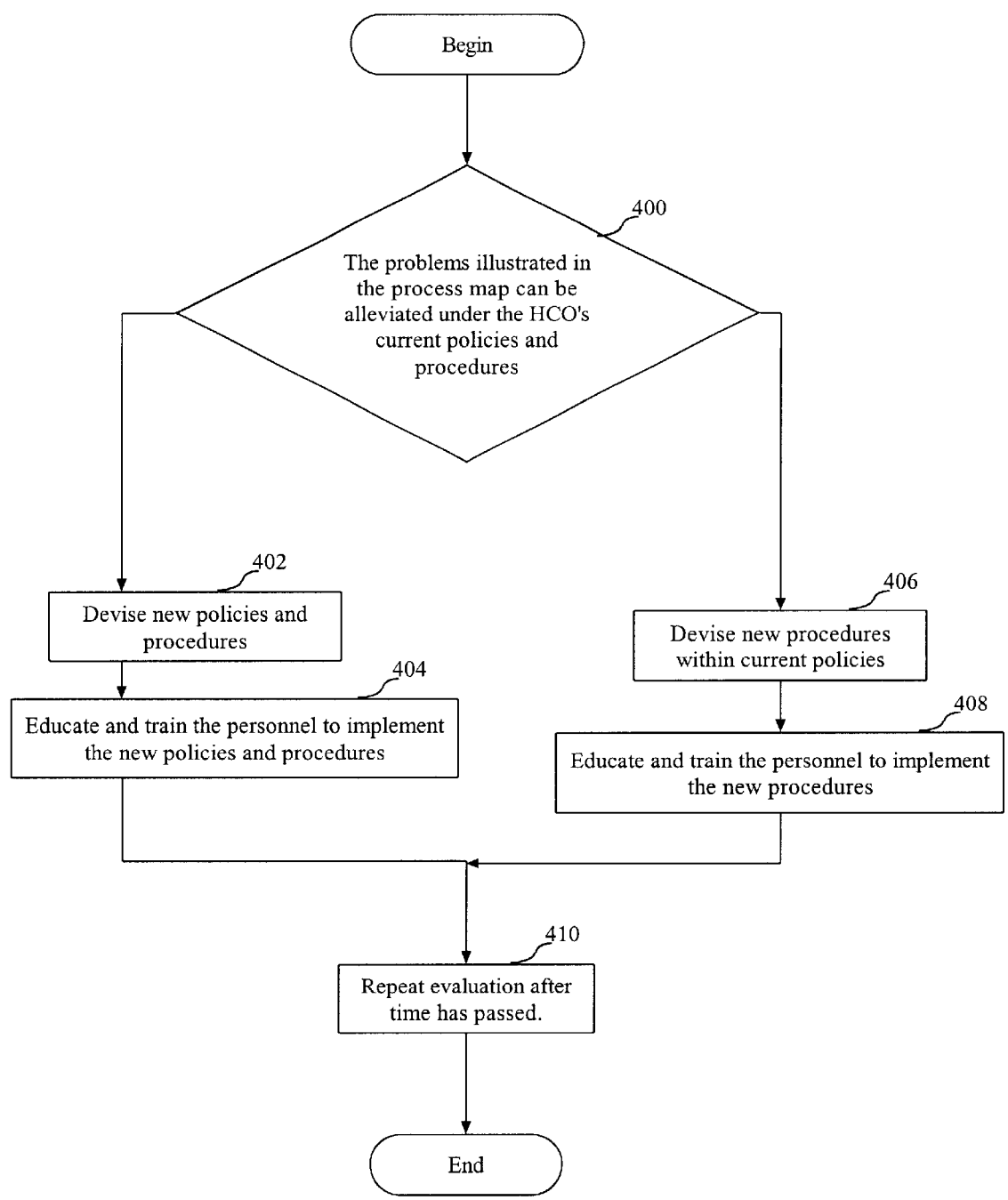
FIG. 4 is a flowchart of the method of improving the dissemination practices of a health care organization.

Using the list of what information each discipline needs for each function within the ICU, questions are formulated for the ICU staff based on the list 300, as shown in FIG. 3. These questions are used in focus groups with the ICU staff to determine how information that is received by the various individuals reaches them from the HCO's entry points 302. After the first focus group, new questions are formulated for subsequent focus groups 304. The new questions are used in focus groups with both the ICU staff and the HCO's staff outside of the ICU in order to determine the path that medical ethical information follows from entering the HCO 306. New questions are formulated 304 subsequent to each focus group for additional focus groups 306 until enough detail is obtained to generate a detailed process map of the information flow within the ICU for informed consent.

The next step in solving the problems illustrated in the process maps is to determine whether the problem is the HCO's policies and procedures or if the problems can be alleviated within the HCO's current policies and procedures 400. If the problem is with the HCO's policies and procedures, then the policies and procedures are modified 406 in order that the medical ethical information reaches the correct people. Otherwise, new procedures are added to the HCO's current policies and procedures 408. This may involve training personnel at the entry points of the medical ethical information to classify the information and to forward it to the appropriate list of discipline and function within the proper department 404 or 408. Another option would be to have all medical ethical information entering the HCO sent to a particular person from the entry points for classification and distribution.

While the invention has been described with reference to an exemplary embodiments various additions, deletions, substitutions, or other modifications may be made without departing from the spirit or scope of the invention. Accordingly, the invention is not to be considered as limited by the foregoing description, but is only limited by the scope of the appended claims.

What is claimed as new and desired to be protected by Letters Patent of the United States is:

1. A method performed on a computer for of evaluating the flow of medical ethical information within a health care organization comprising the steps of:

determining the functions of said health care organization;

determining what medical ethical information said health care organization must distribute;

determining which disciplines and which functions should receive each piece of medical ethical information;

determining what information each individual is actually receiving;

determine the current dissemination practices; and generating a process map of the current dissemination practices.

2. The method as in claim 1, wherein said process map is used to improve said dissemination practices.

3. The method as in claim 2, wherein said dissemination practices are evaluated to determine if any problems illustrated in said process map can be alleviated within said health care organization's current policies and procedures or if the policies and procedures are the problem.

4. The method as in claim 3, wherein if said policies and procedures are determined to be the problem, said policies and procedures are modified.

5. The method as in claim 4, where said health care organization's personnel are educated and trained to implement said modified policies and procedures.

6. The method as in claim 3, wherein if said problems can be alleviated within said health care organization's current policies and procedures, additional procedures are devised to alleviate said problem.

7. The method as in claim 6, wherein said health care organization's personnel are trained to implement said additional procedures.

8. A method for evaluating the flow of medical ethical information within a health care organization comprising:

providing a computer system, said system comprising:
   a microprocessor;
   a user interface coupled to said microprocessor;
   a display coupled to said microprocessor; and
   a data storage area;

storing in said data storage area medical ethical information classified by discipline and function;

inputting into said computer system information representing dissemination practices of said medical ethical information within said health care organization; and generating a process map based on said input of said dissemination practices.

9. The method as in claim 8, further comprising the steps of entering at said user interface a request for said stored medical ethical information for a specific discipline and function and in response, said microprocessor retrieves said information from said data storage area and displays said information on said display.

10. The method as in claim 8, further comprising the step of storing discipline and function information for health care organization employees in said data storage area.

11. The method as in claim 10, further comprising the steps of entering new medical ethical information, and its corresponding discipline and function classification, into said data storage area, and in response, said microprocessor automatically displaying on said display a distribution list for said new medical ethical information.

12. The method as in claim 8, wherein said step of storing said medical ethical information in said data storage area further comprises classifying said information by geographical location.

* * * * *